United States Patent [19]

Goli

[11] Patent Number: 6,020,179
[45] Date of Patent: Feb. 1, 2000

[54] NUCLEIC ACIDS ENCODING HUMAN TYROSINE PHOSPHATASES

[75] Inventor: Surya K. Goli, Sunnyvale, Calif.

[73] Assignee: Incyte Pharmaceuticals, Inc., Palo Alto, Calif.

[21] Appl. No.: 08/725,532

[22] Filed: Oct. 3, 1996

[51] Int. Cl.$^7$ .............................. C12N 9/16; C12N 15/12
[52] U.S. Cl. ..................... 435/196; 536/23.5; 435/69.1; 435/325; 435/320.1; 435/252.3; 435/254.11
[58] Field of Search ..................... 435/69.1, 325, 435/252.3, 254.11, 320.1, 196; 536/23.5

[56] References Cited

PUBLICATIONS

Charbonneau, H., et al., "1002 Protein Phosphatases?" *Annu. Rev. Cell Biol.*, 8:463–93 (1992).
Diamond, R.H., et al., "PRL–1, a Unique Nuclear Protein Tyrosine Phosphatase, Affects Cell Growth" *Mol. and Cell. Biol.*, 14:3752–3762 (1994).
Montagna, M., et al., "A 100–kb physical and transcriptional map around the EDH17B2 gene: identification of three novel genes and a pseudogene of a human homologue of the rat PRL–1 tyrosine phosphatase" *Hum Genet*, 96:532–538 (1995).
Hillier, L., et al., (GI 889096), GenBank Sequence Database (Accession H20401), National Center for Biotechnology Information, National Library of Medicine, Bethesda, Maryland 20894.
Crowell, P.L. et al., "Prenylation of novel oncogenic human $PTP_{CAAX}$ protein phosphatases", Abstract #3952, Proceedings of the American Association for Cancer Research, 1996.
Rommens, J.M. et al., "Generation of a Transcription Map at the HSD17B Locus Centromeric to BRCA1 at 17q21" *Genomics* (1995) 28:530–542.
Hillier, L. et al., (Accession Number N68341) EMBL Database, EMBL Database, Geneva, Switzerland.
Auffray, C. et al., (Accession Number Z43070) EMBL Database, EMBL Database, Geneva, Switzerland.
Cates, C.A. et al., "Prenylation of oncogenic human $PTP_{CAAX}$ protein tyrosine phosphatases" *Cancer Letters* (1996) 110:49–55.

*Primary Examiner*—Sally P. Teng
*Attorney, Agent, or Firm*—Sheela Mohan-Peterson; Lucy J. Billings; Incyte Pharmaceuticals, Inc.

[57] ABSTRACT

The present invention provides novel human protein tyrosine phosphatases (HPTP) and polynucleotides which identify and encode HPTP. The invention provides for genetically engineered expression vectors and host cells comprising the nucleic acid sequences encoding HPTP and for a method of producing HPTP. The invention also provides for pharmaceutical compositions comprising HPTP or antagonists of HPTP, and antibodies which specifically bind HPTP. Additionally, the invention provides antisense molecules to HPTP for treatment or prevention of diseases associated with abnormal expression of HPTP.

5 Claims, 11 Drawing Sheets

```
                     9          18          27        * 36          45          54
5' NTT TTT TTT TTT TTT TTT TTT TTT TGA TGA TAA ATG CAT GTC
        63          72          81          90          99         108
   ATT ATT TAT TTA GAT GTT TCA GCT CTC GCA CTA AGT TTT TAC AAG CTG GTG AAC
       117         126         135         144         153         162
   ACT GAC AAA ATT ATT TCT CCC ACA GAA CTA TAA CCA CAC ATC CCC AGA CAG TAT
       171         180         189         198         207         216
   AAA TAT ATG GTT GAA CTA ACA TTA ATA CAC ATC ACC ATT TTA TCA ATT ACA TAA
       225         234         243         252         261         270
   TAA AAC TTG TCA AGT ATC CAA ATA TTA AGT TAC ACA GCT CAA AAG GCA TAT
       279         288         297         306         315         324
   AAA ATA TTA GAT GTC TGC TCA ATT CAT TAG CAG AAA CCC ATT TCT TTT TTT GCA
       333         342         351         360         369         378
   AGA GAG GTT GGG AAG GAA AAA AAA AAT TTC ACT TTC AAA CAA AAA TAA GTT GGT
       387         396         405         414         423         432
   AAA CAC ACT TCT GAT AAG TAT GGG AAA AAA ATT ACA GGA TTT CAG GAA GTT TAT
       441         450         459         468         477         486
   GGT TAC AAT AAC AAG GCA TCT CTA CCT TTT AAA AAA TAT TTT ACT AAT TAA AGG
```

FIGURE 1A

```
      495       504       513       522       531       540
GCA TTT CTA CAT GTT TKC TRC WGT GCA AGG GCA CCW TTT GCT AAG ATT TAT TGA 549       558       567       576       585       594
TTG TTT TTT TTT TCA CTT TCC CCA TCA CAC TCA CAC GNA CGN TCA CAC TTT TTA 603       612       621       630       639       648
TTT GCC ATA ATG AAC CGC CCA GCT CCT GTG GAA GTC ACA TAC AAG AAC ATG AGA
     F   L   I   T   H   N   R   P   A   P   V   E   V   T   Y   K   N   M   R 657       666       675       684       693       702
TTT CTT ATT ACA CAC AAT CCA ACC ACA ATA ACG ACC TTA AAC AAA TTT ATA GAG GAA
     F   L   I   T   H   N   P   T   N   A   T   L   N   K   F   I   E   E 711       720       729       738       747       756
CTT AAG TAT GGA GTT ACC ACA ATA GTA AGA GTA TGT GAA GCA ACT TAT GAC
     L   K   Y   G   V   T   T   I   V   R   V   C   E   A   T   Y   D 765       774       783       792       801       810
ACT ACT CTT GTG GAG AAA GAA ATC CAT GTT CTT GAT TGG CCT TTT GAT GAT
     T   T   L   V   E   K   E   I   H   V   L   D   W   P   F   D   D 819       828       837       846       855       864
GGT GCA CCA CCA TCC AAC CAG ATT GTT GAT GAC TGG TTA AGT CTT GTG AAA ATT
     G   A   P   P   S   N   Q   I   V   D   D   W   L   S   L   V   K   I
```

FIGURE 1B

```
       873         882         891         900         909         918
AAG TTT CGT GAA GAA CCT GGT TGT TGT ATT GCT GTT CAT TGC GTT GCA GGC CTT
 K   F   R   E   E   P   G   C   C   I   A   V   H   C   V   A   G   L 927         936         945         954         963         972
GGG AGA GCT CCA GTA CTT GTT GCC CTA GCA TTA ATT GAA GGT GGA ATG AAA TAC
 G   R   A   P   V   L   V   A   L   A   L   I   E   G   G   M   K   Y 981         990         999        1008        1017        1026
GAA GAT GCA GTA CAA TTC ATA AGA CAA AAG CGG GGA GCT TTT AAC AGC AAG
 E   D   A   V   Q   F   I   R   Q   K   R   G   A   F   N   S   K 1035        1044        1053        1062        1071        1080
CAA CTT CTG TAT TTG GAG ANG TAT CGT CCT AAA ATG CGG CTG CGT TTC AAA GAT
 Q   L   L   Y   L   E   X   Y   R   P   K   M   R   L   R   F   K   D 1089        1098        1107        1116        1125        1134
TCC AAC GGT CAT AGA AAC AAC TGT TGC ATT CAA TAA AAT TGG GGT GCC TAA TGC
 S   N   G   H   R   N   N   C   C   I   Q   *   N   W   G   A   *   C 1143        1152        1161        1170        1179        1188
TAC TGG AAG TGG RAC TTG AGA TAG GGC CTA ATT TTG TTA TAC CAT ATT AGC CAA 1197        1206        1215        1224        1233        1242
CAT GTT GGC TTA GTA AGT CTA ATG AAG CTT CCA TAG GGG TAT TNA AAG GCA GTT 1251        1260        1269
TTN CCA GGC CTC AAG CTA GAC AGA TTT TNC AAT G 3'
```

FIGURE 1C

```
      9          18       27       36       45       54
5' NNT TTG GAG TTG CCC GCT TTA CTT TGG TTG GGT TGG GGG CGG CGG GCT GTT
                                                                        108
      63       72       81       90       99
   TTG TTC CTT TTC TTT AAG AGT TGG GTT TTC TTT AAT TAT CCA AAC AGT
                                                                        162
      117      126      135      144      153
   GGG CAG CTT CCT CCC CCA CAC CCA AGT ATT TGC ACA ATA TTT GTG CGG GGT ATG
                                                                        216
      171      180      189      198      207
   GGG GTG GGT TTT TAA ATC TCG TTT CTC TTG GAC AAG CAC AGG GAT CTC GTT CTC
                                                                        270
      225      234      243      252      261
   CTC ATT TTT TGG GGG TGT GTG GGG ACT TCT CAG GTC TCC CCA GCC TTC TCT
                                                                        324
      279      288      297      306      315
   GCA GTC CCT TCT GCC CTG CCG GGC CCG TCG GGA GGC GCC ATG GCT CGG ATG AAC
                                                       M   A   R   M   N
                                                                        378
      333      342      351      360      369
   CGC CCG GCC CCG GTG GAG GTG AGC TAC AAA CAC ATG CGC TTC CTC ATC ACC CAC
    R   P   A   P   V   E   V   S   Y   K   H   M   R   F   L   I   T   H
                                                                        432
      387      396      405      414      423
   AAC CCC ACC AAC GCC ACG CTC AGC ACC TTC ATT GAG GAC CTG AAG AAG TAC GGG
    N   P   T   N   A   T   L   S   T   F   I   E   D   L   K   K   Y   G
```

```
     441             450             459             468             477             486
GCT  ACC  ACT  GTG  GTG  CGT  GTG  TGT  GAA  GTG  ACC  TAT  GAC  AAA  ACG  CCG  CTG  GAG
 A    T    T    V    V    R    V    C    E    V    T    Y    D    K    T    P    L    E 495             504             513             522             531             540
AAG  GAT  GGC  ATC  ACC  GTT  GTG  GTG  GAC  TGG  CCG  TTT  GAC  GAT  GGG  GCG  CCG  CCC
 K    D    G    I    T    V    V    V    D    W    P    F    D    D    G    A    P    P 549             558             567             576             585             594
GGC  AAG  GTA  GTG  GAA  GAC  TGG  CTG  AGC  CTG  GTG  AAG  GCC  AAG  TTC  TGT  GAG  GCC
 G    K    V    V    E    D    W    L    S    L    V    K    A    K    F    C    E    A 603             612             621             630             639             648
CCC  GGC  AGC  TGC  GCT  GTG  CAC  GTG  TGC  GTG  GCG  GGC  CTG  GGC  CGG  GCT  CCA  GTC
 P    G    S    C    A    V    H    V    C    V    A    G    L    G    R    A    P    V 657             666             675             684             693             702
CTT  GTG  GCG  CTG  GCC  CTT  ATT  GAG  AGC  GGG  ATG  AAG  TAC  GAG  GAC  GCC  ATY  CAG
 L    V    A    L    A    L    I    E    S    G    M    K    Y    E    D    A    I    Q 711             720             729             738             747             756
TTT  ATS  CGC  CAG  AAG  GGA  CGC  GGA  GCC  ATC  AAC  AGC  AAG  CAG  AAG  CTC  ACC  CTG
 F    X    R    Q    K    G    R    G    A    I    N    S    K    Q    K    L    T    L 765             774             783             792             801             810
GAG  AAA  TAC  CGG  CCC  AAA  CAG  AGG  CTG  CGG  TTC  AAA  GAC  CCA  CAC  ACG  CAC  AAG
 E    K    Y    R    P    K    Q    R    L    R    F    K    D    P    H    T    H    K
```

```
     819         828         837         846         855         864
ACC CGG TGC TGC GTT ATG TAG CTC AGG ACC TTG GCT GGG CCT GGT CGT CAT GTA
 T   R   C   C   V   M 873         882         891         900         909         918
GGT CAG GAC CTT GGC TGG ACC TGG AGG CCC TGC CCA GCC CTG CTC TGC CCA GCC 927         936         945         954         963         972
CAG CAG GGG CTC CAG GCC TTG GNT GGC CCC ATA TCG NNT TTT CCT CNN CNA TAC

981
TNC NGN GAT TTG 3'
```

FIGURE 2C

| Library | Lib Description | Abun | Pct Abun |
|---|---|---|---|
| PINENOM01 | pineal gland, M/F, NORM, WM | 1 | 0.1520 |
| SCORNON01 | spinal cord, 71 M, NORM | 1 | 0.1379 |
| MPHGNOT03 | macrophages (adher PBMNC), M/F | 9 | 0.1162 |
| CORNNOT01 | corneal fibroblasts, 76y | 1 | 0.0999 |
| KERANOT01 | keratinocytes, neonatal M | 4 | 0.0911 |
| OVARTUT01 | ovarian tumor, 43 F, match to OVARNOT03 | 2 | 0.0646 |
| COLNNOT13 | colon, ascending, 28 M | 2 | 0.0621 |
| BEPINOT01 | bronchial epithelium, primary cell line, 54 M | 2 | 0.0609 |
| COLNFET02 | colon, fetal F | 4 | 0.0571 |
| TESTNOT01 | testis, 37 M | 1 | 0.0470 |
| THP1PLB01 | THP-1 promonocyte cell line, treated PMA, LPS | 1 | 0.0452 |
| MUSCNOT01 | muscle, skeletal | 1 | 0.0444 |
| COLNNOT08 | colon, 60 M | 1 | 0.0426 |
| TMLR2DT01 | lymphocytes (non-adher PBMNC), M/F, 24-hr MLR | 2 | 0.0422 |
| LATRTUT02 | heart tumor, myoma, 43 M | 3 | 0.0412 |
| MYOMNOT01 | uterus, myometrium, 43 F | 1 | 0.0409 |
| CARDNOT01 | heart, 65 M | 1 | 0.0399 |
| LIVRNOT01 | liver, 49 M | 2 | 0.0396 |
| MUSCNOT02 | muscle, psoas, 12 M | 1 | 0.0382 |
| SINTTUT01 | small intestine tumor, 42 M | 1 | 0.0382 |
| TLYMNOR01 | lymphocytes (non-adher PBMNC), 24 M, RP | 1 | 0.0372 |
| PLACNOM03 | placenta, fetal, NORM, WM | 1 | 0.0362 |
| NEUTFMT01 | granulocytes, periph blood, M/F, treated fMLP | 2 | 0.0349 |
| LUNGNOT01 | lung, 72 M | 1 | 0.0338 |

FIGURE 3A

| | | | |
|---|---|---|---|
| LNODNOT02 | lymph nodes, 42 F | 1 | 0.0335 |
| THP1NOB01 | THP-1 promonocyte cell line, control | 1 | 0.0327 |
| PROSTUT01 | prostate tumor, 50 M, match to PROSNOT02 | 1 | 0.0310 |
| BLADTUT02 | bladder tumor, 80 F, match to BLADNOT03 | 1 | 0.0305 |
| BRSTTUT03 | breast tumor, 58 F, match to BRSTNOT05 | 2 | 0.0296 |
| COLNNOT16 | colon, 62 M, match to COLNTUT03 | 1 | 0.0295 |
| COLNNOT05 | colon, 40 M, match to COLNCRT01 | 1 | 0.0289 |
| PROSNOT11 | prostate, 28 M | 1 | 0.0282 |
| LUNGNOT12 | lung, 78 M | 1 | 0.0278 |
| COLNNOT22 | colon, 56 F | 1 | 0.0277 |
| BEPINON01 | bronchial epithelium, primary cell line, 54 M, NORM | 1 | 0.0274 |
| BRAITUT01 | brain tumor, oligoastrocytoma, 50 F | 2 | 0.0269 |
| LUNGNOM01 | lung, 72 M, WM | 1 | 0.0267 |
| PENITUT01 | penis tumor, carcinoma, 64 M | 1 | 0.0267 |
| PROSTUT09 | prostate tumor, 66 M | 1 | 0.0264 |
| LUNGNOT14 | lung, 47 M | 1 | 0.0259 |
| COLNPOT01 | colon polyp, 40 F | 1 | 0.0256 |
| LIVRNOM01 | liver, 49 M, WM | 1 | 0.0254 |
| PROSNOT16 | prostate, 68 M | 1 | 0.0250 |
| MMLR1DT01 | macrophages (adher PBMNC), M/F, 24-hr MLR | 1 | 0.0236 |
| THYRNOT01 | thyroid, 64 F | 1 | 0.0228 |
| COLNNOT01 | colon, 75 M, match to COLNTUT02 | 1 | 0.0213 |
| BRSTNOT01 | breast, 56 F | 1 | 0.0192 |
| HNT2AGT01 | hNT2 cell line, post-mitotic neurons | 1 | 0.0190 |
| BRAINOT03 | brain, 26 M | 1 | 0.0185 |
| LUNGNOT04 | lung, 2 M | 1 | 0.0183 |
| PLACNOT02 | placenta, fetal F | 1 | 0.0168 |

FIGURE 3B

| | | | |
|---|---|---|---|
| SINTBST01 | small intestine, ileum, Crohn's, 18 F | 1 | 0.0168 |
| PLACNOM02 | placenta, neonatal F, NORM, WM | 3 | 0.0167 |
| NEUTGMT01 | granulocytes, periph blood, M/F, treated GM-CSF | 1 | 0.0156 |
| BRSTNOT05 | breast, 58 F, match to BRSTTUT03 | 1 | 0.0154 |
| LUNGFEM01 | lung, fetal, NORM, WM | 1 | 0.0148 |
| BRAITUT08 | brain tumor, astrocytoma, 47 M | 1 | 0.0147 |
| BRSTNOT03 | breast, 54 F, match to BRSTTUT02 | 1 | 0.0147 |
| THYRNOT03 | thyroid tumor, adenoma, 28 F | 1 | 0.0138 |
| UCMCL5T01 | mononuclear cells, treated IL-5 | 1 | 0.0125 |
| PROSNOT06 | prostate, 57 M, match to PROSTUT04 | 1 | 0.0114 |
| MELANOM01 | melanocytes, M, NORM, WM | 1 | 0.0096 |
| LUNGFET03 | lung, fetal F | 2 | 0.0091 |
| BRAINOM01 | brain, infant F, NORM, WM | 2 | 0.0089 |

FIGURE 3C

| Library | Lib Description | Abun | Pct Abun |
|---|---|---|---|
| LVENNOT02 | heart, left ventricle, 39 M | 1 | 0.2088 |
| PITUNOT03 | pituitary, 46 M | 2 | 0.0697 |
| SYNORAT05 | synovium, knee, rheumatoid, 62 F | 2 | 0.0572 |
| BRAITUT07 | brain tumor, left frontal, 32 M | 2 | 0.0517 |
| GBLATUT01 | gall bladder tumor, 78 F | 2 | 0.0483 |
| PROSNOT15 | prostate, 66 M, match to PROSTUT10 | 2 | 0.0483 |
| CARDNOT01 | heart, 65 M | 1 | 0.0399 |
| STOMTUT01 | stomach tumor, 52 M, match to STOMNOT02 | 1 | 0.0368 |
| LNODNOT02 | lymph nodes, 42 F | 1 | 0.0335 |
| BRSTTUT02 | breast tumor, 54 F, match to BRSTNOT03 | 1 | 0.0298 |
| UTRSNOT05 | uterus, 45 F | 1 | 0.0278 |
| PROSTUT08 | prostate tumor, 60 M, match to PROSNOT14 | 1 | 0.0266 |
| LUNGNOT10 | lung, fetal M | 1 | 0.0261 |
| PROSNOT18 | prostate, hyperplasia, 58 M | 1 | 0.0256 |
| STOMFET01 | stomach, fetal F | 1 | 0.0255 |
| TMLR3DT02 | lymphocytes (non-adher PBMNC), M/F, 72-hr MLR | 1 | 0.0245 |
| RATRNOT02 | heart, right atrium, 39 M | 1 | 0.0236 |
| HNT2AGT01 | hNT2 cell line, post-mitotic neurons | 1 | 0.0190 |
| SINTBST01 | small intestine, ileum, Crohn's, 18 F | 1 | 0.0168 |
| BRAITUT03 | brain tumor, astrocytoma, 17 F | 1 | 0.0153 |
| LUNGFEM01 | lung, fetal, NORM, WM | 1 | 0.0148 |
| BRAITUT08 | brain tumor, astrocytoma, 47 M | 1 | 0.0147 |
| PROSTUT04 | prostate tumor, 57 M, match to PROSNOT06 | 1 | 0.0117 |
| MELANOM01 | melanocytes, M, NORM, WM | 1 | 0.0096 |

FIGURE 5

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 170 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY:
      (B) CLONE: Consensus (xi) SEQUENCE DESCRIPTION: SEQ ID NO:1:

```
Met Asn Arg Pro Ala Pro Val Glu Val Thr Tyr Lys Asn Met Arg Phe
  1               5                  10                  15

Leu Ile Thr His Asn Pro Thr Asn Ala Thr Leu Asn Lys Phe Ile Glu
             20                  25                  30

Glu Leu Lys Lys Tyr Gly Val Thr Thr Ile Val Arg Val Cys Glu Ala
         35                  40                  45

Thr Tyr Asp Thr Thr Leu Val Glu Lys Glu Gly Ile His Val Leu Asp
     50                  55                  60

Trp Pro Phe Asp Asp Gly Ala Pro Pro Ser Asn Gln Ile Val Asp Asp
 65                  70                  75                  80

Trp Leu Ser Leu Val Lys Ile Lys Phe Arg Glu Glu Pro Gly Cys Cys
                 85                  90                  95
```

```
Ile Ala Val His Cys Val Ala Gly Leu Gly Arg Ala Pro Val Leu Val
            100                 105                 110

Ala Leu Ala Leu Ile Glu Gly Gly Met Lys Tyr Glu Asp Ala Val Gln
        115                 120                 125

Phe Ile Arg Gln Lys Arg Arg Gly Ala Phe Asn Ser Lys Gln Leu Leu
    130                 135                 140

Tyr Leu Glu Xaa Tyr Arg Pro Lys Met Arg Leu Arg Phe Lys Asp Ser
145                 150                 155                 160

Asn Gly His Arg Asn Asn Cys Cys Ile Gln
            165                 170
```

(2) INFORMATION FOR SEQ ID NO:2:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

```
TTTTTTTTTT TTTTTTTTTT TTTTTTTTTT TTTTTTGATG ATAAATGCAT GTCATTATTT    60

ATTTAGATGT TTCAGCTCTC GCACTAAGTT TTTACAAGCT GGTGAACACT GACAAAATTA   120

TTTCTCCCAC AGAACTATAA CCACACATCC CCAGACAGTA TAAATATATG GTTGAACTAA   180

CATTAATACA CATCACCATT TTATCAATTA CATAATAAAA CAAATTGTCA AGTATCCAAA   240

TATTAAGTTA CACAGCTCAA AAGGCATATA AAATATTAGA TGTCTGCTCA ATTCATTAGC   300

AGAAACCCAT TTCTTTTTTT GCAAGAGAGG TTGGGAAGGA AAAAAAAAAT CACACTTTCA   360

AACAAAAATA AGTTGGTAAA CACACTTCTG ATAAGTATGG GAAAAAAATT ACAGGATTTC   420

AGGAAGTTTA TGGTTACAAT AACAAGGCAT CTCTACCTTT TAAAAAATAT TTTACTAATT   480

AAAGGGCATT TCTACATGTT TKCTRCWGTG CAAGGGCACC WTTTGCTAAG ATTTATTGAT   540

TGTTTTTTTT TTCACTTTCC CCATCACACT CACANGNACG NTCACACTTT TTATTTGCCA   600

TAATGAACCG CCCAGCTCCT GTGGAAGTCA CATACAAGAA CATGAGATTT CTTATTACAC   660

ACAATCCAAC CAATGCGACC TTAAACAAAT TTATAGAGGA ACTTAAGAAG TATGGAGTTA   720

CCACAATAGT AAGAGTATGT GAAGCAACTT ATGACACTAC TCTTGTGGAG AAAGAAGGTA   780

TCCATGTTCT TGATTGGCCT TTTGATGATG GTGCACCACC ATCCAACCAG ATTGTTGATG   840

ACTGGTTAAG TCTTGTGAAA ATTAAGTTTC GTGAAGAACC TGGTTGTTGT ATTGCTGTTC   900

ATTGCGTTGC AGGCCTTGGG AGAGCTCCAG TACTTGTTGC CCTAGCATTA ATTGAAGGTG   960

GAATGAAATA CGAAGATGCA GTACAATTCA TAAGACAAAA GCGGCGTGGA GCTTTTAACA  1020

GCAAGCAACT TCTGTATTTG GAGANGTATC GTCCTAAAAT GCGGCTGCGT TTCAAAGATT  1080

CCAACGGTCA TAGAAACAAC TGTTGCATTC AATAAAATTG GGGTGCCTAA TGCTACTGGA  1140

AGTGGRACTT GAGATAGGGC CTAATTTTGT TATACCATAT TAGCCAACAT GTTGGCTTAG  1200

TAAGTCTAAT GAAGCTTCCA TAGGGGTATT NAAAGGCAGT TTTNCCAGGC CTCAAGCTAG  1260

ACAGATTTTN CAATG                                                  1275
```

(2) INFORMATION FOR SEQ ID NO:3:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE: Consensus (xi) SEQUENCE DESCRIPTION: SEQ ID NO:3:

Met Ala Arg Met Asn Arg Pro Ala Pro Val Glu Val Ser Tyr Lys His
 1               5                  10                  15

Met Arg Phe Leu Ile Thr His Asn Pro Thr Asn Ala Thr Leu Ser Thr
            20                  25                  30

Phe Ile Glu Asp Leu Lys Lys Tyr Gly Ala Thr Thr Val Val Arg Val
        35                  40                  45

Cys Glu Val Thr Tyr Asp Lys Thr Pro Leu Glu Lys Asp Gly Ile Thr
 50                  55                  60

Val Val Asp Trp Pro Phe Asp Asp Gly Ala Pro Pro Gly Lys Val
65                  70                  75                  80

Val Glu Asp Trp Leu Ser Leu Val Lys Ala Lys Phe Cys Glu Ala Pro
                85                  90                  95

Gly Ser Cys Val Ala Val His Cys Val Ala Gly Leu Gly Arg Ala Pro
            100                 105                 110

Val Leu Val Ala Leu Ala Leu Ile Glu Ser Gly Met Lys Tyr Glu Asp
        115                 120                 125

Ala Ile Gln Phe Xaa Arg Gln Lys Gly Arg Gly Ala Ile Asn Ser Lys
    130                 135                 140

Gln Leu Thr Tyr Leu Glu Lys Tyr Arg Pro Lys Gln Arg Leu Arg Phe
145                 150                 155                 160

Lys Asp Pro His Thr His Lys Thr Arg Cys Cys Val Met
                165                 170

(2) INFORMATION FOR SEQ ID NO:4:

(i) SEQUENCE CHARACTERISTICS:
        (A) LENGTH: 982 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:4:

TTTGGAGTTG CCCGCTTTAC TTTGGTTGGG TTGGGGGGGG CGGCGGGCTG TTTTGTTCCT      60

TTTCTTTTTT AAGAGTTGGG TTTTCTTTTT TAATTATCCA AACAGTGGGG AGCTTCCTCC     120

CCCACACCCA AGTATTTGCA CAATATTTGT GCGGGGTATG GGGGTGGGTT TTTAAATCTC     180

GTTTCTCTTG GACAAGCACA GGGATCTCGT TCTCCTCATT TTTTGGGGGT GTGTGGGGAC     240

TTCTCAGGTC GTGTCCCCAG CCTTCTCTGC AGTCCCTTCT GCCCTGCCGG GCCCGTCGGG     300

AGGCGCCATG GCTCGGATGA ACGCCCCGGC CCCGGTGGAG GTGAGCTACA AACACATGCG     360

CTTCCTCATC ACCCACAACC CCACCAACGC CACGCTCAGC ACCTTCATTG AGGACCTGAA     420

GAAGTACGGG GCTACCACTG TGGTGCGTGT GTGTGAAGTG ACCTATGACA AAACGCCGCT     480

```
GGAGAAGGAT GGCATCACCG TTGTGGACTG GCCGTTTGAC GATGGGCGC  CCCCGCCCGG    540

CAAGGTAGTG GAAGACTGGC TGAGCCTGGT GAAGGCCAAG TTCTGTGAGG CCCCCGGCAG    600

CTGCGTGGCT GTGCACTGCG TGGCGGGCCT GGGCCGGGCT CCAGTCCTTG TGGCGCTGGC    660

CCTTATTGAG AGCGGGATGA AGTACGAGGA CGCCATYCAG TTTATSCGCC AGAAGGGACG    720

CGGAGCCATC AACAGCAAGC AGCTCACCTA CCTGGAGAAA TACCGGCCCA AACAGAGGCT    780

GCGGTTCAAA GACCCACACA CGCACAAGAC CCGGTGCTGC GTTATGTAGC TCAGGACCTT    840

GGCTGGGCCT GGTCGTCATG TAGGTCAGGA CCTTGGCTGG ACCTGGAGGC CCTGCCCAGC    900

CCTGCTCTGC CCAGCCCAGC AGGGGCTCCA GGCCTTGGNT GGCCCCATAT CGNNTTTTCC    960

TCNNCNATAC TNCNGNGATT TG                                             982
```

(2) INFORMATION FOR SEQ ID NO:5:

(i) SEQUENCE CHARACTERISTICS:
        (A) LENGTH: 167 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 894159

(xi) SEQUENCE DESCRIPTION: SEQ ID NO:5:

```
Met Asn Arg Pro Ala Pro Val Glu Ile Ser Tyr Glu Asn Met Arg Phe
 1               5                  10                  15

Leu Ile Thr His Asn Pro Thr Asn Ala Thr Leu Asn Lys Phe Thr Glu
            20                  25                  30

Glu Leu Lys Lys Tyr Gly Val Thr Thr Leu Val Arg Val Cys Asp Ala
        35                  40                  45

Thr Tyr Asp Lys Ala Pro Val Glu Lys Glu Gly Ile His Val Leu Asp
    50                  55                  60

Trp Pro Phe Asp Asp Gly Ala Pro Pro Asn Gln Ile Val Asp Asp
65                  70                  75                  80

Trp Leu Asn Leu Leu Lys Thr Lys Phe Arg Glu Glu Pro Gly Cys Cys
                85                  90                  95

Val Ala Val His Cys Val Ala Gly Leu Gly Arg Ala Pro Val Leu Val
            100                 105                 110

Ala Leu Ala Leu Ile Glu Cys Gly Met Lys Tyr Glu Asp Ala Val Gln
        115                 120                 125

Phe Ile Arg Gln Lys Arg Arg Gly Ala Phe Asn Ser Lys Gln Leu Leu
    130                 135                 140

Tyr Leu Glu Lys Tyr Arg Pro Lys Met Arg Leu Arg Phe Arg Asp Thr
145                 150                 155                 160

Asn Gly His Cys Cys Val Gln
                165
```

(2) INFORMATION FOR SEQ ID NO:6:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE:

-continued

```
      (vii) IMMEDIATE SOURCE:
            (A) LIBRARY: GenBank
            (B) CLONE: 530162

(xi) SEQUENCE DESCRIPTION: SEQ ID NO:6:

Met Ala Arg Met Asn Arg Pro Ala Pro Val Glu Val Thr Tyr Lys Asn
 1               5                  10                  15

Met Arg Phe Leu Ile Thr His Asn Pro Thr Asn Ala Thr Leu Asn Lys
                20                  25                  30

Phe Ile Glu Glu Leu Lys Lys Tyr Gly Val Thr Thr Ile Val Arg Val
            35                  40                  45

Cys Glu Ala Thr Tyr Asp Thr Thr Leu Val Glu Lys Glu Gly Ile His
        50                  55                  60

Val Leu Asp Trp Pro Phe Asp Asp Gly Ala Pro Pro Ser Asn Gln Ile
65                  70                  75                  80

Val Asp Asp Trp Leu Ser Leu Val Lys Ile Lys Phe Arg Glu Glu Pro
                85                  90                  95

Gly Cys Cys Ile Ala Val His Cys Val Ala Gly Leu Gly Arg Ala Pro
                100                 105                 110

Val Leu Val Ala Leu Ala Leu Ile Glu Gly Gly Met Lys Tyr Glu Asp
            115                 120                 125

Ala Val Gln Phe Ile Arg Gln Lys Arg Arg Gly Ala Phe Asn Ser Lys
        130                 135                 140

Gln Leu Leu Tyr Leu Glu Lys Tyr Arg Pro Lys Met Arg Leu Arg Phe
145                 150                 155                 160

Lys Asp Ser Asn Gly His Arg Asn Asn Cys Cys Ile Gln
                165                 170
```

NUCLEIC ACIDS ENCODING HUMAN TYROSINE PHOSPHATASES

FIELD OF THE INVENTION

The invention relates to nucleic acid and amino acid sequences of two novel disease associated protein tyrosine phosphatases and to the use of these sequences in the diagnosis, study, prevention, and treatment of disease.

BACKGROUND OF THE INVENTION

Phosphatases remove phosphate groups from molecules previously activated by kinases and control most cellular signaling events that regulate cell growth and differentiation, cell-to-cell contacts, the cell cycle and oncogenesis. Protein phosphorylation is the ubiquitous strategy used to control the activities of eukaryotic cells. It is estimated that more than 1000 of the 10,000 proteins active in a typical mammalian cell are phosphorylated. The high energy phosphate which confers activation is transferred from adenosine triphosphate molecules to a protein by protein kinases, and is subsequently removed from the protein by protein phosphatases.

There appear to be three, evolutionarily-distinct protein phosphatase gene families (Carbonneau H and Tonks NK (1992, Annu Rev Cell Biol 8:463–93). They are the protein phosphatases (PP), the protein tyrosine phosphatases (PTP) and the acid/alkaline phosphatases (AP). Although APs dephosphoryate substrates in vitro, their role in vivo is not well known.

PTPs remove phosphate groups only from selected phosphotyrosines on particular types of proteins. In so doing, PTPs reverse the effects of protein tyrosine kinases (PTK) and therefore play a significant role in cell cycle and cell signaling processes. PTPs possess a high specific enzyme activity relative to their PTK counterparts and therefore ensure that tyrosine phosphorylations are very short lived and very uncommon in resting cells. Many PTKs are encoded by oncogenes, and it is well known that oncogenesis is often accompanied by increased tyrosine phosphorylation activity. It is therefore possible that PTPs may serve to prevent or reverse cell transformation and the growth of various cancers by controlling the levels of tyrosine phosphorylation in cells. This is supported by studies showing that overexpression of PTP can suppress transformation in cells and, conversely, specific inhibition of PTP can enhance cell transformation.

The PTPs are found in transmembrane, receptor-like and nontransmembrane, non-receptor forms, and possess a diversity in size (20 kDa to greater than 100 kDa) and structure. All PTPs share homology within a region of 240 residues which delineates the catalytic domain and contain a conserved sequence, e.g., residues 99 through 107 of SEQ ID NO:5 or residues 102 through 110 of SEQ ID NO:6, near the carboxy terminus. The combination of the catalytic domain with a wide variety of structural motifs accounts for the diversity and specificity of these enzymes. In the nonreceptor isoforms, the noncatalytic sequences may also confer different modes of regulation and target PTPs to various intracellular compartments.

Receptor-like PTPs (R-PTPs) are generally large (greater than 100 kDa) and are grouped on the basis of their single transmembrane segment and two, tandem PTP domains within the cytoplasmic tail. In contrast to the similarity within the internal cytoplasmic domains of these molecules, there is considerable diversity among the extraceliular segement. Key examples of this type of PTP are CD45, a PTP found on the surface of leucocytes that helps to activate T and B lymphocytes when activated by extracellular antibodies and LAR, a PTP having structural features related to the N-CAM family of cell adhesion molecules on its extracellular domain and which may be involved in cell adhesion processes.

Nonreceptor PTPs (NR-PTP) are generally smaller (about 50 kDa) than the R-PTPs and have single catalytic domains and noncatalytic sequences of variable length positioned at either the N- or C-termini. NR-PTPs are intracellular and may use their noncatalytic sequences to direct them to particular subcellular compartments or to determine their enzyme regulating activity. Some NR-PTPs may be divided into subfamilies based on similarities in their noncatalytic domains. For example, human PTPH1 and MEG01 contain homologous catalytic domains and N-terminal segments with homology to band 4.1, talin and ezrin. In addition they are thought to be localized between actin stress fibers and the plasma membrane where they modulate cytoskeletal dynamics. T-cell PTP and PTP1β display a high degree of similarity in their catalytic domains and structural similarities in their C-terminal noncatalytic domains that may help direct them to membranes where they regulate enzyme activity.

Recently, a new class of smaller (about 20 kDa) NR-PTPs has been found which have a single catalytic domain and are represented by PRL-1, found in regenerating rat liver and hepatoma cells, and OV-1, found in human ovarian tissue (Diamond R H, et al (1994) Mol Cell Biol 14:3752–62; Montagna M et al (1995) Hum Genet 96: 532–538). These PTPs possess homology to other NR-PTPs only within the region of the catalytic active site. Stably transfected cells that overexpress PRL-1 exhibit altered cell growth and morphology and a transformed phenotype. Furthermore, it is postulated that PRL-1 is important in the control of normal cell growth and in the development of tumorigenicity.

It is apparent that PTPs may serve either as positive or negative regulators of cell growth, and that a detailed understanding of phosphatase interaction in signal transduction pathways should reveal many potential mechanisms to provide the means for clinical diagnosis or therapeutic intervention in the progression of cancer, inflammatory illnesses, or oncogenesis. The discovery of new PTPs may satisfy a need in the art by providing agents which are useful for the prevention or treatment of HPTP-1-associated diseases.

SUMMARY OF THE INVENTION

The invention discloses two novel disease associated protein tyrosine phosphatases hereinafter referred to as HPTP-1 and HPTP-2 and collectively as HPTP. These two proteins share features with two nontransmembrane PTPs involved in regulating cell growth. Accordingly, the invention features substantially purified HPTP, as shown in the amino acid sequences of SEQ ID NOs:1 and 3. The invention also features a method for producing HPTP.

One aspect of the invention features isolated and substantially purified polynucleotides which encode HPTP. In a particular aspect, the polynucleotides are the nucleotide sequences of SEQ ID NOs:2 and 4. In addition, the invention features polynucleotide sequences that hybridize under stringent conditions to SEQ ID NOs:2 and 4.

The invention further relates to the nucleic acid sequences encoding HPTP, oligonucleotides, peptide nucleic acids, fragments, portions or antisense molecules thereof. The invention also relates to an expression vector containing the nucleic acid sequences encoding HPTP, and which can be used to transform host cells or organisms. The invention also provides for the use of similar vectors for therapeutic transformation of cells to prevent proliferation of cancerous cells or tissues.

The invention also relates to antibodies which bind specifically to HPTP.

BRIEF DESCRIPTION OF THE FIGURES

FIGS. 1A, 1B, and 1C show the amino acid sequence (SEQ ID NO:1) and nucleic acid sequence (SEQ ID NO:2) of the novel HPTP-1 of the present invention produced using MACDNASIS PRO software (Hitachi Software Engineering Co Ltd, San Bruno, Calif.).

FIGS. 2A, 2B, and 2C similarly show the amino acid sequence (SEQ ID NOS:3A, 3B and 3C) and nucleic acid sequence (SEQ ID NO:4) of the novel HPTP-2 of the present invention.

FIG. 3 shows the northern analysis for the consensus nucleotide sequence (SEQ ID NO:2) produced electronically using the LIFESEQ™ database (Incyte Pharmaceuticals, Palo Alto, Calif.).

FIG. 4 similarly shows the northern analysis for the consensus nucleotide sequence (SEQ ID NO:4)

FIG. 5 shows the amino acid sequence alignments among HPTP-1 (SEQ ID NO:1), HPTP-2 (SEQ ID NO:3), GI 894159 human PTP, OV-1 (SEQ ID NO:5) and GI 530162 rat PTP, PRL-1 (SEQ ID NO:6) (Diamond et al, supra; Montagna et al, supra). Sequences were aligned using the multisequence alignment program of DNASTAR software (DNAStar Inc, Madison, Wis.).

DESCRIPTION OF THE INVENTION

Definitions

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Consensus" as used herein may refer to a nucleic sequence 1) which has been resequenced to resolve uncalled bases, 2) which has been extended using XL-PCR kit (Perkin Elmer) in the 5' or the 3' direction and resequenced, 3) which has been assembled from overlapping sequences of more than one Incyte clone (GCG fragment assembly system, GCG" Madison, Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary strand of nucleic acid (Nielsen P E et al (1993) Anticancer Drug Des 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HPTP.

A "substitution" results from the replacement of one or more nucleotides or amino acids by different nucleotides or amino acids, respectively.

As used herein, HPTP refers to the amino acid sequence of substantially purified HPTP obtained from any species, particularly mammalian, including bovine, ovine, porcine, murine, equine, and preferably human, from any source whether natural, synthetic, semi-synthetic or recombinant.

A "variant" of HPTP is defined as an amino acid sequence which differs by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to HPTP having structural, regulatory or biochemical functions of a naturally occurring HPTP. Likewise, "immunologically active" defines the capability of the natural, recombinant or synthetic HPTP, or any oligopeptide thereof, to induce a specific immune response in appropriate animals or cells and to bind with specific antibodies.

The term "derivative" as used herein refers to the chemical modification of a nucleic acid encoding HPTP or the encoded HPTP. Illustrative of such modifications would be replacement of hydrogen by an alkyl, acyl, or amino group. A nucleic acid derivative would encode a polypeptide which retains essential biological characteristics of natural HPTP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

The term "hybridization" as used herein shall include "any process by which a strand of nucleic acid joins with a complementary strand through base pairing" (Coombs J (1994) *Dictionary of Biotechnology*, Stockton Press, New York, N.Y.). Amplification is defined as the production of additional copies of a nucleic acid sequence and is generally carried out using polymerase chain reaction technologies well known in the art (Dieffenbach C W and G S Dveksler (1995) *PCR Primer, a Laboratory Manual*, Cold Spring Harbor Press, Plainview, N.Y.).

"Stringency" typically occurs in a range from about Tm−5° C. (5° C. below the Tm of the probe) to about 20° C. to 25° C. below Tm. As will be understood by those of skill in the art, stringent hybridization can be used to identify or detect identical polynucleotide sequences or to identify or detect similar or related polynucleotide sequences.

PREFERRED EMBODIMENTS

The present invention relates to novel human protein tyrosine phosphatases (HPTP) identified among the cDNAS from a library constructed from skeletal muscle tissue (HPTP-1) and from stomach tumor tissue (HPTP-2) and to the use of the nucleic acid and amino acid sequences in the study, diagnosis, prevention and treatment of disease.

The consensus nucleotide sequence SEQ ID NO: 2, disclosed herein, was extended and assembled from Incyte Clones 121894 (MUSCNOT01), 352438 (LVENNOT01), 383710 (HYPONOB01), 459667 (KERANOT01), 479994 (LIVRBCT01), 646834 (BRSTTUT02), 716720

(PROSTUT01), 900738 (BRSTTUT03), 911770 (STOMNOT02), 1373206 (BSTMNON02), and 1443250 (THYRNOT03).

The consensus nucleotide sequence SEQ ID NO: 4, disclosed herein, was extended and assembled from Incyte Clones 490222 (HNT2AGT01), 504976 (TMLR3DT02), 534687 (LVENNOT02), 540462 (LNODNOT02), 646402 (BRSTTUT02), 889096 (STOMTUT01), 945318 (RATRNOT02), 1261554 (SYNORAT05), and 1263105 (SYNORAT05).

As shown in FIGS. 3A, 3B, and 3C cDNAs encoding portions of HPTP-1 were found in a variety of tumor tissues including ovarian, heart, small intestine, prostate, bladder, brain and thyroid tumors. They were also found in various cells and tissues related to the immune system or systemic defense including macrophages, lymphocytes and granuloyctes. Similarly, FIG. 4 shows that cDNAs encoding a portion of HPTP-2 were also found in a variety of tumor tissues including brain, stomach, breast, and prostate tumor, in rheumatoid tissue and in lymphocytes. It must be noted that naturally occurring expression of HPTP is not necessarily limited to these cells and tissues.

The present invention also encompasses HPTP variants. A preferred HPTP variant is one having at least 80% amino acid sequence similarity to the amino acid sequence (SEQ ID NO:1), a more preferred HPTP variant is one having at least 90% amino acid sequence similarity to SEQ ID NOs:1 and 3 and a most preferred HPTP variant is one having at least 95% amino acid sequence similarity to SEQ ID NOs:1 and 3.

Figure 5:
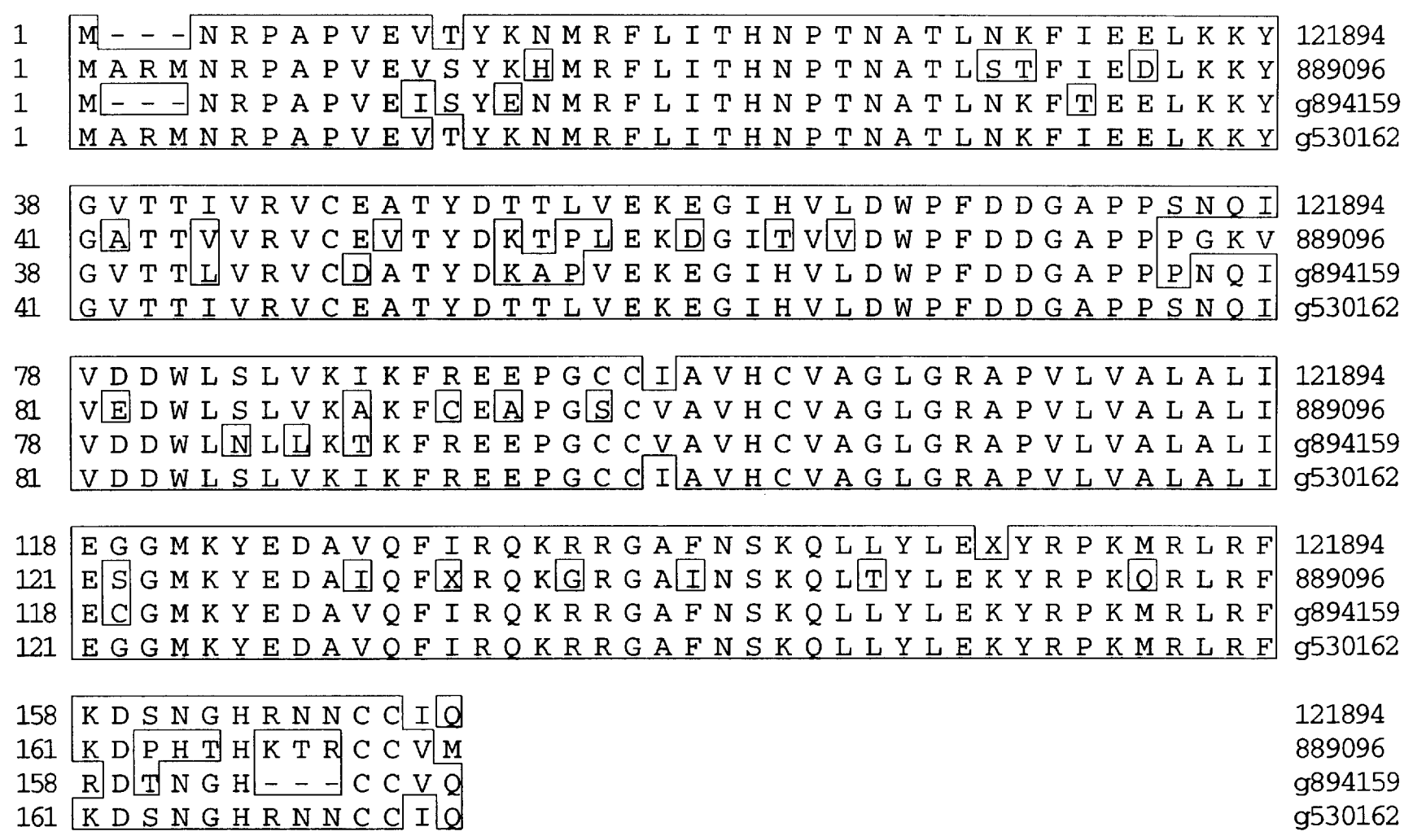

Nucleic acid encoding a portion of HPTP-1 of the present invention was first identified in cDNA, Incyte Clone 121894 (SEQ ID NO:2), through a computer-generated search for amino acid sequence alignments. Similarly, nucleic acid encoding a portion of HPTP-2 was first identified in Incyte Clone 889096. The nucleic acid sequence, SEQ ID NO:2, encodes the 170 amino acid sequence, SEQ ID NO:1, while the nucleic acid sequence SEQ ID NO: 4 encodes the 173 amino acid sequence, SEQ ID NO: 3. The present invention is based, in part, on the chemical and structural homology among HPTP-1, HPTP-2, and the known PTPs rat PRL-1(GI 530162; SEQ ID NO: 6) and human OV-1 (GI 889096; SEQ ID NO: 5). FIG. 5 illustrates the close sequence identity among the four molecules. In particular, a motif common to all classes of PTPs, is found from about residue 99 through about residue 107 of SEQ ID NO:1 for HPTP-1 and is identical for all four molecules shown as well as the following 11 residues. Also, the carboxy terminus of these four PTPs all contain the following residues R(131), Q(142), and L(143) common to other PTPs (cf Diamond et al, supra).

The HPTP Coding Sequences

The extended and assembled nucleic acid and deduced amino acid sequences of HPTP are shown in FIGS. 1A, 1B, 1C, and 2A, 2B, 2C. In accordance with the invention, any nucleic acid sequence which encodes HPTP can be used to generate recombinant molecules which express HPTP. In a specific embodiment described herein, a partial sequence encoding HPTP-1 was first isolated as Incyte Clone 121894 from a skeletal muscle cDNA library (MUSCNOT01), and for HPTP-2 as Incyte Clone 889096 from a stomach tumor library (STOMTUT01).

It will be appreciated by those skilled in the art that as a result of the degeneracy of the genetic code, a multitude of HPTP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring HPTP, and all such variations are to be considered as being specifically disclosed.

Although nucleotide sequences which encode HPTP and its variants are preferably capable of hybridizing to the nucleotide sequence of the naturally occurring sequence under appropriately selected conditions of stringency, it may be advantageous to produce nucleotide sequences encoding HPTP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HPTP and its derivatives without altering the encoded amino acid sequences include the production of RNA transcripts having more desirable properties, such as a greater half-life, than transcripts produced from the naturally occurring sequence.

A DNA sequence, or portions thereof, encoding HPTP or its derivative may be produced entirely by synthetic chemistry. After synthesis, the gene may be inserted into any of the many available DNA vectors and cell systems using reagents that generally available. Moreover, synthetic chemistry may be used to introduce mutations into a sequence encoding HPTP or any portion thereof.

Also included within the scope of the present invention are polynucleotide sequences that are capable of hybridizing to the nucleotide sequences of SEQ ID NOs:2 and 4 under various conditions. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego, Calif.) incorporated herein by reference, and on the salt concentrations under which the steps of the process are carried out.

Altered nucleic acid sequences encoding HPTP which may be used in accordance with the invention include deletions, insertions or substitutions of different nucleotides resulting in a polynucleotide that encodes the same or a functionally equivalent HPTP. The protein may also show deletions, insertions or substitutions of amino acid residues which produce a silent change and result in a functionally equivalent HPTP. Deliberate amino acid substitutions may be made on the basis of similarity in polarity, charge, solubility, hydrophobicity, hydrophilicity, and/or the amphipathic nature of the residues as long as the biological activity of HPTP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding HPTP. As used herein, an "allele" or "allelic sequence" is an alternative form of the nucleic acid sequence encoding HPTP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing may be used which are well known in the art and employ such enzymes as the Klenow fragment of DNA polymerase I, SEQUENASE DNA polymerase (US Biochemical Corp, Cleveland, Ohio)), Taq polymerase (Perkin Elmer, Norwalk, Conn.), thermostable T7 polymerase (Amersham, Chicago, Ill.), or combinations of recombinant polymerases and proofreading exonucleases such as the ELONGASE amplification system (GIBCO/BRL, Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI 377 DNA sequencers (Perkin Elmer).

Extending the Polynucleotide Sequence

The polynucleotide sequence encoding HPTP may be extended utilizing partial nucleotide sequence and various methods known in the art to detect upstream sequences such as promoters and regulatory elements. For example, Gobinda et al (1993; PCR Methods Applic 2:318–22) use "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO 4.06 primer analysis software 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is walking PCR (Parker J D et al (1991) Nucleic Acids Res 19:3055–60), which involves targeted gene walking. Alternatively, PCR, nested primers, PROMOTER-FINDER libraries (Clontech, Palo Alto, Calif.) and PromoterFinder libraries can be used to walk in genomic DNA. This process avoids the need to screen libraries and is useful in finding intron/exon junctions.

Preferred libraries for screening for full length cDNAs are those which have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton, Calif.), and other companies. Capillary sequencing may employ flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. GENOTYPER and SEQUENCE NAVIGATOR software from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode HPTP, fragments of the polypeptide, fusion proteins or functional equivalents thereof may be used in recombinant DNA molecules that direct the expression of HPTP in appropriate host cells. Due to the inherent degeneracy of the genetic code, other DNA sequences which encode substantially the same or a functionally equivalent amino acid sequence, may be used to clone and express HPTP. As will be understood by those of skill in the art, it may be advantageous to produce HPTP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HPTP expression or to produce recombinant RNA transcripts having desirable properties, such as a longer half-life, than transcripts produced from naturally occurring sequence.

The nucleotide sequences of the present invention can be engineered in order to alter HPTP-encoding sequences for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant HPTP-encoding sequence may be ligated to a heterologous sequence to encode a fusion protein. For example, for screening of peptide libraries for inhibitors of HPTP activity, it may be useful to encode a chimeric HPTP protein that is recognized by a commercially available antibody. A fusion protein may also be engineered to contain a cleavage site located between HPTP and the heterologous protein sequence, so that the HPTP may be cleaved and substantially purified away from the heterologous moiety.

In an alternate embodiment of the invention, the sequence encoding HPTP may be synthesized, whole or in part, using chemical methods well known in the art (see Caruthers M H et al (1980) Nuc Acids Res Symp Ser 215–223, Horn T et al(1980) Nuc Acids Res Symp Ser 7:225–232, etc). Alternatively, the protein itself may be produced using chemical methods to synthesize an amino acid sequence for HPTP, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, WH Freeman and Co, New York, N.Y.). The composition of the synthetic peptides may be confirmed by amino acid analysis or sequencing (eg, the Edman degradation procedure; Creighton, supra). Additionally the amino acid sequence of HPTP, or any part thereof, may be altered during direct synthesis and/or combined using chemical methods with sequences from other proteins, or any part thereof, to produce a variant polypeptide.

Expression Systems

In order to express a biologically active HPTP, the nucleotide sequence encoding HPTP or its functional equivalent, is inserted into an appropriate expression vector, ie, a vector which contains the necessary elements for the transcription and translation of the inserted coding sequence.

Methods which are well known to those skilled in the art can be used to construct expression vectors containing a sequence encoding HPTP and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview, N.Y. and Ausubel F M et al (1989) *Current Protocols in Molecular Biology*, John Wiley & Sons, New York, N.Y.

A variety of expression vector/host systems may be utilized to contain and express a sequence encoding HPTP. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of the sequence encoding HPTP, vectors based on SV40 or EBV may be used with an appropriate selectable marker.

In bacterial systems, a number of expression vectors may be selected depending upon the use intended for HPTP. For example, when large quantities of HPTP are needed for the induction of antibodies, vectors which direct high level expression of fusion proteins that are readily purified may be desirable. Such vectors include, but are not limited to, the multifunctional *E. coli* cloning and expression vectors such as BLUESCRIPT phagemid (Stratagene), in which the sequence encoding HPTP may be ligated into the vector in frame with sequences for the amino-terminal Met and the subsequent 7 residues of β-galactosidase so that a hybrid protein is produced; pIN vectors (Van Beeke & Schuster (1989) J Biol Chem 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HPTP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York, N.Y., pp 191–196 or Weissbach and Weissbach (1988) *Methods for Plant Molecular Biology*, Academic Press, New York, N.Y., pp 421–463.

An alternative expression system which may be used to express HPTP is an insect system. In one such system, *Autographa californica* nuclear polyhedrosis virus (AcNPV) is used as a vector to express foreign genes in *Spodoptera frugiperda* cells or in Trichoplusia larvae. The sequence encoding HPTP may be cloned into a nonessential region of the virus, such as the polyhedrin gene, and placed under control of the polyhedrin promoter. Successful insertion of the sequence encoding HPTP will render the polyhedrin gene inactive and produce recombinant virus lacking coat protein coat. The recombinant viruses are then used to infect *S. fruaiperda* cells or Trichoplusia larvae in which HPTP is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a sequence encoding HPTP may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a sequence encoding HPTP. These signals include the ATG initiation codon and adjacent sequences. In cases where the sequence encoding HPTP, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HPTP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisd, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the sequence encoding HPTP is inserted within a marker gene sequence, recombinant cells containing the sequence encoding HPTP can be identified by the absence of marker gene function. Alternatively, a marker gene can be placed in tandem with the sequence encoding HPTP under the control of a single promoter. Expression of the marker gene in response to induction or selection usually indicates expression of the tandem sequence as well.

Alternatively, host cells which contain the sequence encoding HPTP and expressing HPTP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding HPTP can be detected by DNA-DNA or DNA-RNA hybridization or amplification using probes, portions or fragments of the sequence encoding HPTP. Nucleic acid amplification based assays involve the use of oligonucleotides or oligomers based on the nucleic acid sequence to detect transformants containing DNA or RNA encoding HPTP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer. A variety of protocols for detecting and measuring the expression of HPTP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HPTP is preferred, but a competitive binding assay may be employed. These and other assays are described, among other places, in Hampton R et al (1990, *Serological Methods, a Laboratory Manual*, APS Press, St Paul, Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the HPTP-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HPTP

Host cells transformed with a nucleotide sequence encoding HPTP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing sequences encoding HPTP can be designed with signal sequences which direct secretion of HPTP through a prokaryotic or eukaryotic cell membrane. Other recombinant constructions may join the sequence encoding HPTP to nucleotide sequence encoding a polypeptide domain which will facilitate purification of soluble proteins (Kroll D J et al (1993) DNA Cell Biol 12:441–53; cf discussion of vectors infra containing fusion proteins).

HPTP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp, Seattle, Wash.). The inclusion of a cleavable linker sequences such as Factor XA or enterokinase (Invitrogen, San Diego, Calif.) between the purification domain and HPTP is useful to facilitate purification. One such expression vector provides for expression of a fusion protein comprising the sequence encoding HPTP and nucleic acid sequence encoding 6 histidine residues followed by thioredoxin and an enterokinase cleavage site. The histidine residues facilitate purification while the enterokinase cleavage site provides a means for purifying HPTP from the fusion protein.

In addition to recombinant production, fragments of HPTP may be produced by direct peptide synthesis using solid-phase techniques (of Stewart et al (1969) *Solid-Phase Peptide Synthesis*, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A peptide synthesizer (Perkin Elmer, Foster City, Calif.) in accordance with the instructions provided by the manufacturer. Various fragments of HPTP may be chemically synthesized separately and combined using chemical methods to produce the full length molecule.

Uses of HPTP

The rationale for the use of nucleotide and polypeptide sequences disclosed herein is based in part on the chemical and structural homology among the HPTP and the known PTPs. Because of the widespread roles of PTKs and their respective PTPs in cell growth and regulation processes in various cells and tissues, altered HPTP expression may be implicated in a variety of disorders and diseases.

HPTP-1 appears to be associated with inflammatory cells and various cancers, and may therefore have a role in the pathogenesis of diseases such as rheumatoid arthritis and osteoarthritis and carcinomas of the, intestine, bladder, prostate, breast, and brain. HPTP-2 is similarly associated with inflammation and carcinomas of the brain, stomach, breast, and prostate.

HPTP-1 or HPTP-2 may also be used for the treatment or prevention of cancer or inflammatory disease by increasing HPTP activity through the use of gene therapy or administration of HPTP or agonists of HPTP. Alternatively, in cases where overexpression of HPTP may be associated with a disease condition, as with PRL-1, HPTP activity may be decreased by the use of antisense molecules to HPTP, antibodies to HPTP, or antagonists of HPTP. Additionally, the sequences for HPTP will provide the basis for screening for agonists, antagonists or inhibitors that modulate the activity or products of HPTP.

HPTP Antibodies

HPTP-specific antibodies are useful for the diagnosis and treatment of conditions and diseases associated with expression of HPTP. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

It is not necessary that the portion of HPTP used for antibody induction have biological activity; however, the protein fragment, or oligopeptide must be antigenic. Peptides used to induce specific antibodies may have an amino acid sequence consisting of at least five amino acids, and preferably at least 10 amino acids. Preferably, they should mimic a portion of the amino acid sequence of the natural protein and may contain the entire amino acid sequence of a small, naturally occurring molecule. Short stretches of HPTP amino acids may be fused with those of another protein such as keyhole limpet hemocyanin and antibody produced against the chimeric molecule. Procedures well known in the art can be used for the production of antibodies to HPTP.

For the production of antibodies, various hosts including goats, rabbits, rats, mice, etc may be immunized by injection with HPTP or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HPTP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York, N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S.

Pat. No. 4,946,778) can be adapted to produce HPTP-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HPTP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HPTP and its specific antibody and the measurement of complex formation. A two-site, monoclonal-based immunoassay utilizing monoclonal antibodies reactive to two noninterfering epitopes on a specific HPTP protein is preferred, but a competitive binding assay may also be employed. These assays are described in Maddox D E et al (1983, J Exp Med 158:1211).

Diagnostic Assays Using HPTP Specific Antibodies

Particular HPTP antibodies are useful for the diagnosis of conditions or diseases characterized by expression of HPTP or in assays to monitor patients being treated with HPTP, its fragments, agonists or inhibitors. Diagnostic assays for HPTP include methods utilizing the antibody and a label to detect HPTP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HPTP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HPTP is preferred, but a competitive binding assay may be employed. These assays are described, among other places, in Maddox, D E et al (1983, J Exp Med 158:1211).

In order to provide a basis for diagnosis, normal or standard values for HPTP expression must be established. This is accomplished by combining body fluids or cell extracts taken from normal subjects, either animal or human, with antibody to HPTP under conditions suitable for complex formation which are well known in the art. The amount of standard complex formation may be quantified by comparing various artificial membranes containing known quantities of HPTP with both control and disease samples from biopsied tissues. Then, standard values obtained from normal samples may be compared with values obtained from samples from subjects symptomatic of disease. Deviation between standard and subject values establishes the presence of a disease state.

Drug Screening

HPTP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HPTP and the agent being tested, may be measured.

Another technique for drug screening which may be used for high throughput screening of compounds having suitable binding affinity to the HPTP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HPTP and washed. Bound HPTP is then detected by methods well known in the art. Substantially purified HPTP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HPTP specifically compete with a test compound for binding HPTP. In this manner, the antibodies can be used to detect the presence of any peptide which shares one or more antigenic determinants with HPTP.

Uses of the Polynucleotide Encoding HPTP

A polynucleotide sequence encoding HPTP or any part thereof may be used for diagnostic and/or therapeutic purposes. For diagnostic purposes, the sequence encoding HPTP of this invention may be used to detect and quantitate gene expression in biopsied tissues in which HPTP may be expressed in response to oncogenes. The diagnostic assay is useful to distinguish between absence, presence, and excess expression of HPTP and to monitor regulation of HPTP levels during therapeutic intervention. Included in the scope of the invention are oligonucleotide sequences, antisense RNA and DNA molecules, and peptide nucleic acids, (PNA).

Another aspect of the subject invention is to provide for hybridization or PCR probes which are capable of detecting polynucleotide sequences, including genomic sequences, encoding HPTP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring HPTP, alleles or related sequences.

Probes may also be used for the detection of related sequences and should preferably contain at least 50% of the nucleotides from any of these sequences encoding HPTP. The hybridization probes of the subject invention may be derived from the nucleotide sequence of SEQ ID NOs:2 or 4 or from genomic sequence including promoter, enhancer elements and introns of the naturally occurring sequence encoding HPTP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs include the cloning of nucleic acid sequences encoding HPTP or HPTP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding HPTP may be used for the diagnosis of conditions or diseases with which the expression of HPTP is associated. For example, polynucleotide sequences encoding HPTP may be used in hybridization or PCR assays of fluids or tissues from biopsies to detect HPTP expression. The form of such qualitative or quantitative methods may include southern or northern analysis, dot blot or other membrane-based technologies; PCR technologies; dip stick, pin, chip and ELISA technologies. All of these techniques are well known in the art and are the basis of many commercially available diagnostic kits.

The HPTP-encoding nucleotide sequences disclosed herein provide the basis for assays that detect activation or induction associated with inflammation or disease. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding HPTP in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HPTP expression must be established. This is accomplished by combining body fluids or cell extracts taken from normal subjects, either animal or human, with HPTP, or a portion thereof, under conditions suitable for hybridization or amplification. Standard hybridization may be quantified by comparing the values obtained for normal subjects with a dilution series of HPTP run in the same experiment where a known amount of substantially purified HPTP is used. Standard values obtained from normal samples may be compared with values obtained from samples from patients affected by HPTP-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, may be used as described in U.S. Pat. Nos. 4,683, 195 and 4,965,188 provides additional uses for oligonucleotides based upon the sequence encoding HPTP. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 212:229 –236) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

As discussed previously, underexpression or overexpression of PTPs may result in tumorigenesis in different instances. Therefore gene therapy, using a nucleotide sequence encoding HPTP may be useful where increased HPTP activity is needed and, conversely, an antisense molecule to a sequence encoding HPTP may be administered where decreased expression of HPTP is needed.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense of the sequence encoding HPTP. See, for example, the techniques described in Sambrook et al (supra) and Ausubel et al (supra).

The polynucleotides comprising full length cDNA sequence and/or its regulatory elements enable researchers to use the sequence encoding HPTP as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HPTP can be turned off by transfecting a cell or tissue with expression vectors which express high levels of a desired HPTP fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of the sequence encoding HPTP, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco, N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding HPTP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HPTP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in US Pat. Nos. 5,399,493 and 5,437,994, disclosed herein by reference. Delivery by transfection and by liposome are quite well known in the art.

Furthermore, the nucleotide sequences encoding HPTP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding HPTP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York, N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a the sequence encoding HPTP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HPTP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that HPTP can be used to screen for therapeutic molecules which would ameliorate the adverse effects of inflammatory cells in autoimmune diseases.

The examples below are provided to illustrate the subject invention and are not included for the purpose of limiting the invention.

EXAMPLES

I HPTP-1 MUSCNOTO1 cDNA Library Construction and Isolation

The normal skeletal muscle used for this library was obtained from the Keystone Skin Bank, International Institute for the Advancement of Medicine (Exton, Pa.). Five grams of normal skeletal muscle tissue from a 47 year old male was flash frozen, ground in a mortar and pestle, and lysed immediately in buffer containing guanidinium isothiocyanate. Lysis was followed by several phenol chloroform extractions and ethanol precipitation. Poly A$^+$ RNA was isolated using biotinylated oligo d(T) primer and streptavidin coupled to a paramagnetic particle (Promega Corp, Madison. Wis.) and sent to Stratagene (La Jolla, Calif.). Stratagene prepared the cDNA library using oligo d(T) priming. Synthetic adapter oligonucleotides were ligated onto the cDNA molecules enabling them to be inserted into the UNI-ZAP vector system (Stratagene).

The quality of the cDNA library was screened using DNA probes, and then, the pBluescript® phagemid (Stratagene) was excised. Subsequently, the custom-constructed library phage particles were infected into E. coli host strain XL1-BLUE competent cells (Stratagene).

The phagemid forms of individual cDNA clones were obtained by the in vivo excision process, in which the host bacterial strain was coinfected with both the library phage and an fl helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was also purified using the QIAWELL-8 plasmid purification system (QIAGEN Inc, Chatsworth, Calif.). The DNA was eluted from the purification resin and prepared for DNA sequencing and other analytical manipulations.

II HPTP-2 STOMTUTO1 cDNA Library Construction and Isolation

The STOMTUT01 cDNA library was constructed from gastric adenocarcinoma. The donor was a 52 year old Caucasian male who had undergone a total gastrectomy following diagnoses of an invasive grade 4 adenocarcinoma involving the gastroesophageal junction which was accompanied by symptoms of abdominal pain and abnormal loss of weight. As indicated in the pathology report, tumor cells were identified in the muscularis propria and invaded surrounding perigastric adipose tissue. Furthermore, metastases were detected in 6 of 18 epigastric lymph nodes biopsied. Surgical removal was extended to include parts of the duodenum and esophagus and the spleen. Prior to surgery, the patient was being treated with Priloseq® (Omeprazole) to inhibit gastric acid secretion.

The frozen tissue was homogenized and lysed using a Brinkmann POLYTRON homogenizer PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water and DNase treated at 37° C. The RNA extraction was repeated with acid phenol chloroform pH 8.0 and precipitated with sodium acetate and ethanol as before. The mRNA was then isolated using the OLIGOTEX kit (QIAGEN Inc; Chatsworth, Calif.) and used to construct the cDNA library.

The mRNA was handled according to the recommended protocols in the SUPERSCRIPT plasmid system (Cat. #18248-013; Gibco/BRL), cDNAs were fractionated on a SEPHAROSE CL4B column (Cat. #275105-01; Pharmacia), and those cDNAs exceeding 400 bp were ligated into the PSPORT1 plasmid. The plasmid pSport I was subsequently transformed into DH5α™ competent cells (Cat. #18258-012; Gibco/BRL).

Plasmid DNA was released from the cells and purified using the REAL PREP-96 plasmid purification kit (Catalog #26173; QIAGEN, Inc). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

III Sequencing of cDNA Clones

In both MUSCNOTO1 and STOMTUTO1 the cDNAs were sequenced by the method of Sanger F and AR Coulson (1975; J Mol Biol 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

IV Homology Searching of cDNA Clones and Their Deduced Proteins

Each cDNA was compared to sequences in GenBank using a search algorithm developed by Applied Biosystems and incorporated into the INHERIT-670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra). Analogous computer techniques using BLAST (Altschul S F 1993 and 1990, supra) are used to search for identical or related molecules in nucleotide databases such as GenBank or the LIFESEQ™ database (Incyte, Palo Alto, Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search shown in FIGS. 3A, 3B, and 3C and 4 are reported as a list of libraries in which the HPTP encoding sequence occurs. Abundance and percentage abundance of the HPTP encoding sequence are also reported. Abundance directly reflects the number of times a particular transcript is represented in a cDNA library, and percent abundance is abundance divided by the total number of sequences examined in the cDNA library.

VI Extension of the Sequence Encoding HPTP

The nucleic acid sequences of SEQ ID Nos:2 and 4 are used to design oligo-nucleotide primers for extending a partial nucleotide sequence to full length or for obtaining 5' sequence from genomic libraries. One primer is synthesized to initiate extension in the antisense direction (XLR) and the other is synthesized to extend sequence in the sense direction (XLF). Primers allow the extension of the know sequence "outward" generating amplicons containing new, unknown nucleotide sequence for the region of interest (U.S. patent application 08/487,112, filed Jun. 7, 1995, specifically incorporated by reference). The initial primers are designed from the cDNA using OLIGO 4.06 primer analysis software (National Biosciences), or another appropriate program, to be 22–30 nucleotides in length, to have a GC content of 50%, or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; MJ Research, Watertown, Mass.) and the following parameters:

| Step 1  | 94° C. for 1 min (initial denaturation) |
|---------|-----------------------------------------|
| Step 2  | 65° C. for 1 min                        |
| Step 3  | 68° C. for 6 min                        |
| Step 4  | 94° C. for 15 sec                       |
| Step 5  | 65° C. for 1 min                        |
| Step 6  | 68° C. for 7 min                        |
| Step 7  | Repeat step 4–6 for 15 additional cycles |
| Step 8  | 94° C. for 15 sec                       |
| Step 9  | 64° C. for 1 min                        |
| Step 10 | 68° C. for 7:15 min                     |
| Step 11 | Repeat step 8–10 for 12 cycles          |
| Step 12 | 72° C. for 8 min                        |
| Step 13 | 4° C. (and holding)                     |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick DNA purification kit (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec                          |
|--------|--------------------------------------------|
| Step 2 | 94° C. for 20 sec                          |
| Step 3 | 55° C. for 30 sec                          |
| Step 4 | 72° C. for 90 sec                          |
| Step 5 | Repeat steps 2–4 for an additional 29 cycles |
| Step 6 | 72° C. for 180 sec                         |
| Step 7 | 4° C. (and holding)                        |

Aliquots of the PCR reactions are run on agarose gels together with molecular weight markers. The sizes of the PCR products are compared to the original partial cDNAs, and appropriate clones are selected, ligated into plasmid and sequenced.

VII Labeling and Use of Hybridization Probes

Hybridization probes derived from SEQ ID Nos:2 and 4 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 primer analysis software (National Biosciences), labeled by combining 50 pmol of each oligomer and 250 mCi of $[-^{32}P]$ adenosine triphosphate (Amersham, Chicago Ill.) and T4 polynucleotide kinase (DuPont NEN®, Boston Mass.). The labeled oligonucleotides are substantially purified with sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR autoradiography film (Kodak, Rochester, N.Y.) is exposed to the blots or the blots are placed in a PHOIM-AGER cassette (Molecular Dynamics, Sunnyvale, Calif.) for several hours, hybridization patterns are compared visually.

VIII Antisense Molecules

The sequence encoding HPTP, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to a portion of the coding sequence of HPTP as shown in SEQ ID Nos:2 and 4 is used to inhibit expression of the naturally occurring sequence. The complementary oligonucleotide is designed from the most unique 5' sequence and used either to inhibit transcription by preventing promoter binding to the upstream nontranslated sequence or translation of a transcript encoding HPTP by preventing the ribosome from binding. Using an appropriate portion of the leader and 5' sequence of SEQ ID Nos:2 or 4, an effective antisense oligonucleotide includes any 15–20 nucleotides spanning the region which translates into the signal or early coding sequence of the polypeptide as shown in FIGS. 1A, 1B, 1C, or 2A, 2B, 2C.

IX Expression of HPTP

Expression of HPTP is accomplished by subcloning the cDNAs into appropriate vectors and transfecting the vectors into host cells. In this case, the cloning vector, pSport, previously used for the generation of the cDNA library is used to express HPTP in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HPTP. The signal sequence directs the secretion of HPTP into the bacterial growth media which can be used directly in the following assay for activity.

X Assay for HPTP Activity

HPTP activity is measured by the hydrolysis of P-nitrophenyl phosphate (PNPP). HPTP is incubated together with PNPP in HEPES buffer pH 7.5, in the presence of 0.1% β-mercaptoethanol at 37° C. for 60 min. The reaction is stopped by the addition of 6 μl of 10 N NaOH and the increase in light absorbance at 410 nm of the hydrolyzed PNPP is measured using a spectrophotometer (Diamond et al, supra).

XI Production of HPTP Specific Antibodies

HPTP is substantially purified using PAGE electrophoresis (Sambrook, supra) is used to immunize rabbits and to produce antibodies using standard protocols. The amino acid sequence translated from HPTP is analyzed using DNASTAR software (DNAStar Inc) to determine regions of high immunogenicity and a corresponding oligopeptide is synthesized and used to raise antibodies by means known to those of skill in the art. Analysis to select appropriate epitopes, such as those near the C-terminus or in hydrophilic regions is described by Ausubel F M et al (supra).

Typically, the oligopeptides are 15 residues in length, synthesized using an Applied Biosystems 431A peptide sythesizer using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XII Purification of Naturally Occurring HPTP Using Specific Antibodies

Naturally occurring or recombinant HPTP is substantially purified by immunoaffinity chromatography using antibodies specific for HPTP. An immunoaffinity column is constructed by covalently coupling HPTP antibody to an activated chromatographic resin such as CnBr-activated Sepharose (Pharmacia Biotech). After the coupling, the resin is blocked and washed according to the manufacturer's instructions.

Media containing HPTP is passed over the immunoaffinity column, and the column is washed under conditions that allow the preferential absorbance of HPTP (eg, high ionic strength buffers in the presence of detergent). The column is eluted under conditions that disrupt antibody/HPTP binding (eg, a buffer of pH 2–3 or a high concentration of a chaotrope such as urea or thiocyanate ion), and HPTP is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polynucleotide consisting of the sequence of SEQ ID NO:2.

2. An isolated and purified polynucleotide which is completely complementary to the polynucleotide of claim 1.

3. An expression vector comprising the polynucleotide of claim 1.

4. An isolated host cell transformed with the expression vector of claim 3.

5. A method for producing a polypeptide consisting of the amino acid sequence of SEQ ID NO:1, the method comprising the steps of:

a) culturing the host cell of claim 4 under conditions suitable for the expression of the polypeptide; and b) recovering the polypeptide from the host cell culture.

* * * * *